United States Patent
Nyman

[11] Patent Number: 5,571,160
[45] Date of Patent: Nov. 5, 1996

[54] PERMANENTLY CURVED SLEEVE FOR SHAPING AN ELECTRODE CABLE, AND METHOD FOR IMPLANTING THE CABLE WITH THE SLEEVE

[75] Inventor: Per Nyman, Djursholm, Sweden

[73] Assignee: Pacesetter AB, Solna, Sweden

[21] Appl. No.: 272,825

[22] Filed: Jul. 11, 1994

[30] Foreign Application Priority Data

Jul. 22, 1993 [SE] Sweden .................. 9302476

[51] Int. Cl.⁶ ........................................ A61N 1/05
[52] U.S. Cl. ........................................ 607/122
[58] Field of Search ................ 607/115, 116, 607/119, 122, 123, 125, 126; 128/65, 772; 604/95, 280, 281, 282; 606/129

[56] References Cited

U.S. PATENT DOCUMENTS

| | | |
|---|---|---|
| 3,729,008 | 4/1973 | Berkovits . |
| 3,844,292 | 10/1974 | Bolduc .................. 607/126 |
| 3,890,977 | 6/1975 | Wilson . |
| 4,136,703 | 1/1979 | Wittkampf . |
| 4,402,328 | 9/1983 | Doring . |
| 4,585,013 | 4/1986 | Harris .................. 607/126 |
| 4,677,990 | 7/1987 | Neubauer . |
| 5,129,889 | 7/1982 | Hahn et al. ............ 604/280 |
| 5,306,245 | 4/1994 | Heaven ................. 604/280 |

*Primary Examiner*—William E. Kamm
*Attorney, Agent, or Firm*—Hill, Steadman & Simpson

[57] ABSTRACT

A device for shaping an electrode cable, such as a medical electrode cable for use with a pacemaker, includes a substantially tubular element or sleeve, having a length which is relatively short in comparison to the length of the electrode cable. The internal diameter of the tubular element is only slightly larger than the exterior diameter of electrode cable, so that the tubular element can be slid on and off the electrode cable. When the tubular element is on the electrode cable, it surrounds a portion of the electrode cable. The tubular element is curved in a desired manner, and is sufficiently stiff so that the portion of the electrode cable surrounded by the tubular element conforms to the shape of the tubular element. The device is extremely simple and inexpensive and simplifies adaptation of the electrode for placement in a patient's heart.

15 Claims, 2 Drawing Sheets

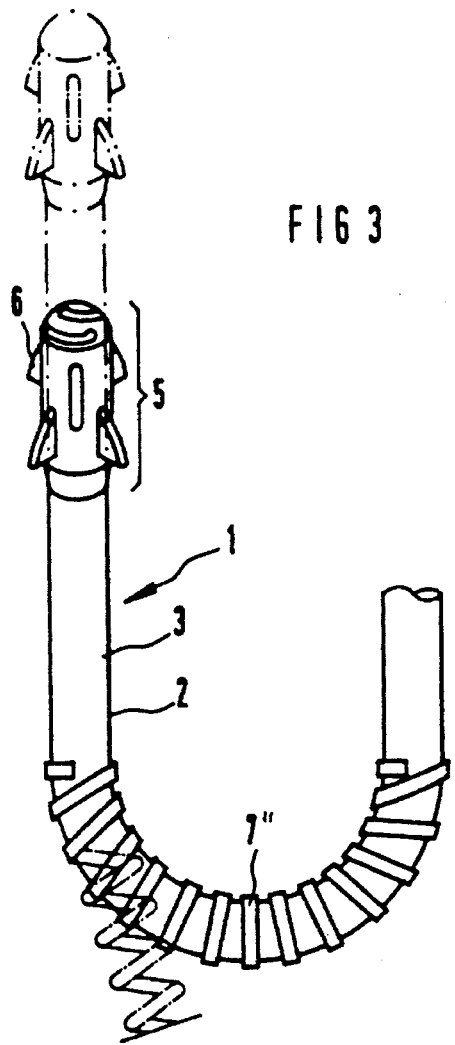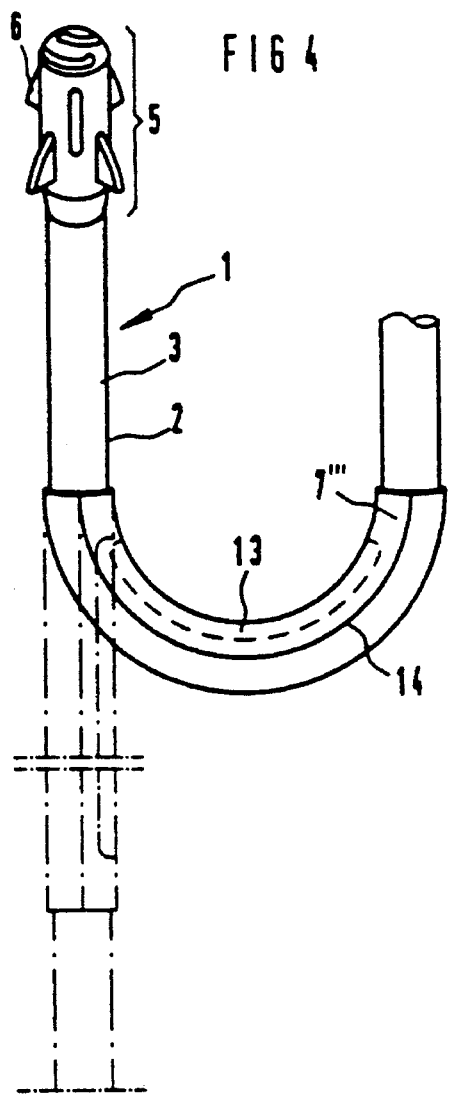

PERMANENTLY CURVED SLEEVE FOR SHAPING AN ELECTRODE CABLE, AND METHOD FOR IMPLANTING THE CABLE WITH THE SLEEVE

BACKGROUND OF THE INVENTION

1. Field of the Invention

The present invention is directed to a device for shaping an electrode cable, such as a medical electrode cable of the type employed with a pacemaker.

2. Description of the Prior Art

The use of J-shaped electrode cables for supporting the electrode tip, used for stimulating the atrial appendage of a patient, and designed to press against the wall of the atrial appendage has long been known. One such electrode device is disclosed in U.S. Pat. No. 4,402,328. Because of the precurved shape of the electrode cable, the electrode head remains in place against the atrial appendage wall, and tends to remain in that position. Another means for shaping an electrode cable is described in U.S. Pat. No. 4,136,703. A relatively stiff tube extending the length of the electrode cable is inserted into the stylet channel of the electrode cable. A J-shaped, precurved stylet is introduced into the tube and is maintained straight by the tube. When the distal end of the electrode cable is inside the heart, the tube is retracted, thereby exposing the stylet which then shapes the distal end of the cable. A disadvantage of this known electrode cable is that it is extremely stiff. If the stylet is removed from the electrode cable, the electrode tip positioned in the atrial appendage would attempt to pull itself out of position, because of the weight of the electrode cable.

A combined electrode and catheter are disclosed in U.S. Pat. No. 3,890,977 having portions thereof consisting of a so-called "shape memory" metal. The shape memory metal components are disposed at specific locations along the electrode-catheter cable. After the cable has been implanted in the heart of a patient, the cable is shaped by the shape memory components assuming a predetermined shape, upon being elevated to a body temperature.

A disadvantage shared by all of the above-described known electrode devices is that they require a large assortment of J-shaped electrode cables and/or precurved stylets of different sizes, because the difference between the bend in the cable and the electrode tip must be adapted, to greater or lesser degrees, to the size of each patient's heart.

SUMMARY OF THE INVENTION

It is an object of the present invention to provide an electrode cable of the type suitable for positioning an electrode tip in a patient's heart for the purpose of stimulating the heart, which facilitates adaptation of the electrode cable to the size and shape of the patient's heart with extreme simplicity and at low cost.

The above object is achieved in accordance with the principles of the present invention in an electrode shaping device which includes a tubular element or sleeve, having a length which is short relative to the length of the electrode cable. The internal diameter of the tubular element or sleeve is only slightly larger than the external diameter of the electrode cable, so that the element or sleeve can be slid on and off the electrode cable. When the tubular element is on the electrode cable, it surrounds a portion of the length of the cable. The tubular element is sufficiently stiff so as to cause the portion of the electrode cable surrounded by the element to be shaped so as to conform to the shape of the element. The tubular element can be arranged at any desired location along the length of the electrode cable, so that an extremely simple and inexpensive means is achieved for adapting a standardized electrode cable to the size and shape of any patient's heart. The physician can simply maintain an inventory of straight, standard electrode cables onto which an element according to the invention can be slid. This simplifies the assortment of electrode cables which are needed to accommodate different heart shapes and sizes, and thus reduces the inventory which a manufacturer, retailer or hospital must maintain.

In a further embodiment of the invention, the tubular element can be precurved, but is still capable of being straightened by means of a control element which is a further component of the device, such as a stylet, so that the electrode cable can be introduced into the heart through a vein in a known manner.

The tubular element may be U-shaped or J-shaped. The latter version permits a standardized J-shaped electrode cable to be achieved.

In a preferred embodiment of the invention, the tubular element may consist at least in part of a shape memory metal, which assumes a desired shape at body temperature. By the use of such material, the element can be arranged on an electrode cable which is introducible into the heart, without the need for a stylet to straighten the electrode cable during implantation. The shape memory metal element, which curves into the desired shape inside the heart, thereby causes the electrode cable to conform to the same shape as well, and can be approximately straight during the implantation phase.

The inner diameter of the tubular element can be selected so as to conform as closely as may be desired to the outer diameter of the electrode cable. The inner diameter of the tubular element may be selected sufficiently larger than the outer diameter of the electrode cable so that the tubular element can be easily slid back and forth on the electrode cable. This makes changing the position of the element relative to the length of the cable quick and simple, with such changes in position also changing the distance between the tubular element and the electrode tip.

In a further embodiment of the invention, the element can be slit along its entire longitudinal length, thereby further facilitating sliding of the element on and off the electrode cable in a fast and simple manner.

In a further version of the above embodiment, the slit at the opposite end regions fo the tubular element can be helically twisted, so as to lock the ends of the tubular element onto the electrode cable.

In a structurally simple version of the invention, the tubular element can be in the form of a coiled spring, making the tubular element very light. The tubular element in this embodiment, due to its coiled shape, can be screwed or twisted on and off of the electrode cable.

DESCRIPTION OF THE DRAWINGS

FIGS. 1–4 are respective side views of an electrode cable shaping element constructed in accordance with the principles of the present invention, in different embodiments.

DESCRIPTION OF THE PREFERRED EMBODIMENTS

Figure 1:
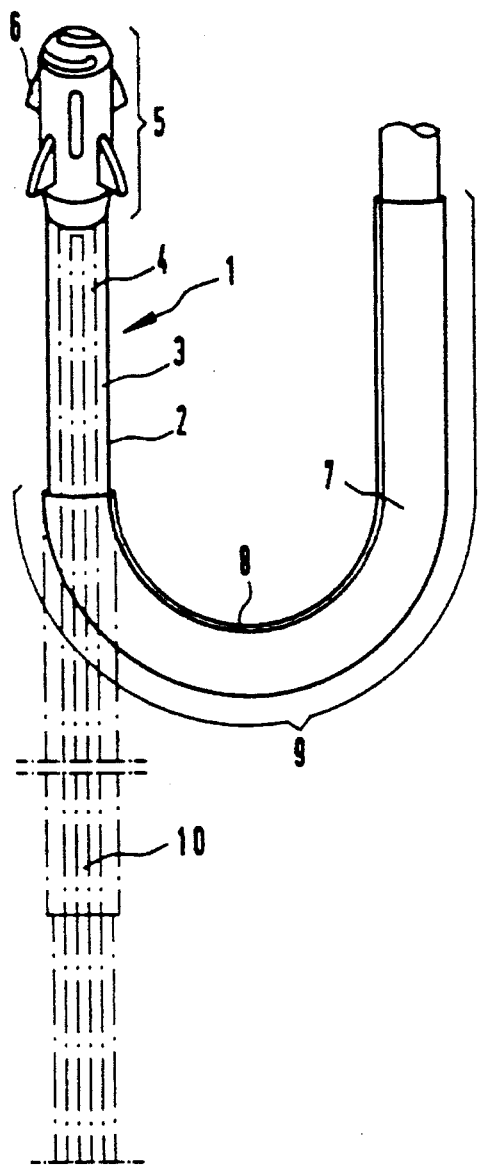

A straight, standard pacemaker electrode 1 is shown in FIG. 1. The electrode 1 consists of an electrode cable 2, containing an elongate, flexible, helical conductor (not shown) and having an exterior covered with a layer of insulation 3. The interior of the helical conductor forms a channel 4. An electrode head 5 for stimulating heart tissue in a patient is disposed at the distal end of the conductor, which is also the distal end of the electrode cable 2. A fin-shaped fixing element 6 is disposed at the electrode head 5 for affixing the electrode 5 to the heart wall. When a physician wishes to use this standard electrode for stimulating the atrial appendage in a patient's heart, the physician slides an element 7 constructed in accordance with the principles of the present invention onto the electrode cable 2.

The element 7, which is designed to shape the electrode cable 2, is essentially tubular and is short relative to the length of the electrode cable 2. The inner diameter of the element 7 is adapted to the external diameter of the electrode cable 2 so that the element 7 can be slid on and off the electrode cable 2. In the embodiment shown in Figure 1, the element 7, having a J-shape in this embodiment, is slit along its entire longitudinal length, as indicated by the slit 8. Arrangement of the element 7 on the electrode cable 2 is thereby facilitated in a simple manner. The element 7 is sufficiently stiff (i.e., it has a rigidity which is higher than the rigidity of the electrode cable2) so that the region 9 of the electrode cable 2 which is covered by the element 7 is caused to conform to the shape of the element 7. Because the element 7 is devised so as to be slidable on the electrode cable 2, the physician can select the required distance between the element 7 an the electrode head 5 which is necessary for proper placement of the head 5 in the heart of the patient in question. The element 7 can be slid on and off the electrode cable 2, so that a correct length is achieved for the area on the electrode cable 2 surrounded by the element 7. The element 7 is sufficient stiff to retain the shape shown in FIG. 1, however, it is still sufficiently pliable so as to be capable of being straightened by means of a stylet 10, introduced into the channel 4, as indicated by the dot-dash representation of the element 7 in FIG. 1. In this manner, the electrode cable 2 can be introduced into the heart through a vein in the conventional manner.

Figure 2:
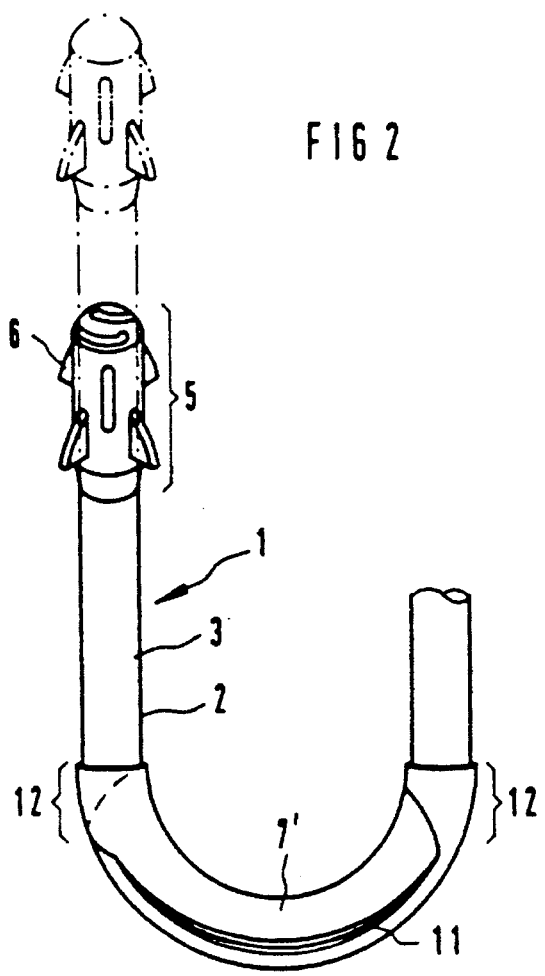

A further embodiment of the shaping element is shown in FIG. 2, wherein the element 7' has a longitudinal slit 11 which is helically twisted at each of the opposite end areas 12 of the element 7'. The helical twist at the ends 12 serves to secure the ends 12 to the cable 2. The dot-dash representation of the electrode head 5 relative to the element 7' shows that the distance between the electrode head 5 and the element 7' can be changed in the manner described above.

An embodiment of the shaping element is shown in FIG. 3 wherein the element 7" has a U-shape, and wherein the element 7" is in the form of a coiled spring having flights with a varying pitch. In the embodiment of FIG. 3, the element 7" can either be screwed onto the electrode cable from the side, as indicated by the dot-dash representation of the element 7" in FIG. 3, or can be slid on or off of the electrode cable 2 from the proximal end of the electrode cable 2, i.e. the end intended for connection to the pacemaker housing. The element 7" in this embodiment can also be slid along the electrode cable 2 so that the distance between the element 7" and the electrode head 5 can be changed, as indicated by the dot-dash representation of the electrode head 5 in FIG. 3. The element 7" in the embodiment of FIG. 3 may be made of a shape memory metal which assumes a desired shape, i.e., a U-shape in this instance, at body temperature. This permits the physician to employ an electrode device 1 which is introducible into the heart through a vein without the need for a stylet, because the element 7" can be straight during the implantation, and will thereafter automatically assume the desired U-shaped inside the heart upon reaching body temperature.

FIG. 4 shows a further embodiment of the shaping element, in the form of a plate 13 made of shape memory metal which, as described in conjunction with FIG. 3, can bend from an approximately straight configuration to a predetermined U-shape, as illustrated in FIG. 4. The element 7''' is also provided with a slit 14 so that it can be threaded on and off the electrode cable 2.

In the embodiments employing shape memory metal for the element 7''', the element 7''' may be made entirely of such material, or may have portions thereof made of such material.

The shaping element in the various embodiments can also be made of a silicone material, either entirely or with portions consisting of shape memory metal. The shaping element may alternatively consist of a resorbable material so as to assist implantation only until the electrode head 5 becomes embedded in the heart wall, and thereafter dissolving. The use of a shaping element consisting of resorbable material permits the electrode cable 5 to achieve a desirable flexibility in the U-shaped area or J-shaped area, after the shaping element has dissolved, which may assist in extending the life of the electrode cable 2 and the conductor therein.

With the present invention, a straight, standard electrode can be provided with an adjustable shaping element 7 or 7' or 7" or 7''' mountable thereon, which quickly converts this standard electrode into a J-shaped electrode, for example, for stimulating an atrial appendage. Additionally, the distance between the U-shaped element 7' or the J-shaped element 7 and the electrode head 5 can be quickly changed, making a simple adaptation of the electrode cable 2 to each individual patient's heart possible. As previously noted, this also permits a simplified assortment of electrode devices to be maintained on hand, and accordingly reduces the inventory for a manufacturer, retailer or hospital.

Although modifications and changes may be suggested by those skilled in the art, it is the intention of the inventors to embody within the patent warranted hereon all changes and modifications as reasonably and properly come within the scope of their contribution to the art.

I claim as our invention:

1. A medical electrode assembly comprising:

an electrode cable having an outer diameter, an exterior surface and a length, for shaping said electrode cable, and a rigidity;

a tubular element having a length which is short relative to the length of said electrode cable and having an inner diameter relative to said outer diameter of said electrode cable permitting said tubular element to be manually placed over said exterior surface of said electrode cable to assume an arbitrarily selectable position along the length of said electrode cable, said tubular element, when on said electrode cable, surrounding a portion of said electrode cable, and said tubular element having a permanently curved shape and having a rigidity which is stronger than said rigidity of said electrode cable for conforming said portion of said electrode cable surrounded by said tubular element to the permanently curved shape of said tubular element.

2. A medical electrode assembly as claimed in claim 1, wherein said electrode cable has a channel therein, and said medical electrode assembly further comprising a stylet insertable into and moveable in said channel in said electrode cable, and wherein said tubular element is precurved and wherein said rigidity of said tubular element permits said tubular element to be temporarily straightened by said stylet when said stylet is inserted into channel in said electrode cable, said tubular element reassuming said permanently curved shape upon removal of said stylet from said channel.

3. A device as claimed in claim 1, wherein said tubular element is U-shaped.

4. A medical electrode assembly as claimed in claim 1, wherein said tubular element is J-shaped.

5. A device as claimed in claim 1, wherein said tubular element has at least a portion thereof consisting of shape memory metal for causing said tubular element to assume said selected shape when reaching body temperature.

6. A medical electrode assembly as claimed in claim 1, wherein said tubular element has an inner diameter relative to said external diameter of said electrode cable to permit said tubular element to be slid back and forth along the length of said electrode cable.

7. A device as claimed in claim 1, wherein said tubular element has a slit along its entire length.

8. A device as claimed in claim 7, wherein said tubular element has opposite ends, and wherein said slit is helically twisted at said opposite ends.

9. A device as claimed in claim 1, wherein said tubular element comprises a coiled spring.

10. A medical electrode assembly as claimed in claim 1, wherein said tubular element consists of a silicone material.

11. A medical electrode assembly as claimed in claim 1, wherein said tubular element consists of a resorbable material.

12. A method for implanting a medical electrode cable comprising the steps of:

selecting a straight electrode cable having an outer diameter, an exterior surface and a length and a pliancy;

selecting a tubular element having a length which is short relative to the length of said electrode cable and having an inner diameter which is less than said outer diameter of said electrode cable and having a permanently curved shape and a rigidity which is stronger than the rigidity of said electrode cable;

manually placing said tubular element over said exterior surface of said electrode cable at an arbitrarily selectable position along the length of said electrode cable so that said tubular element surrounds a portion of said electrode cable, for causing said portion of said electrode cable to conform to the shape of said permanently curved tubular element; and inserting said electrode cable with said tubular element thereon into a vein of a subject.

13. A method as claimed in claim 12 wherein the step of selecting a straight electrode cable comprises selecting a straight electrode cable having an interior channel therein, and said method comprising the additional steps of:

temporarily inserting a stylet into said interior channel of said electrode cable for temporarily straightening said tubular element;

and removing said stylet after inserting said electrode cable with said tubular element thereon in said vein for causing said tubular element to reassume said permanently curved shape.

14. A method as claimed in claim 12 wherein the step of selecting a tubular element comprises selecting a tubular element comprising a hollow element and wherein the step of manually placing said tubular element over said exterior surface of said electrode cable comprises sliding said hollow element onto said exterior surface of said electrode cable until said selected position along the length of said electrode cable is reached.

15. A method as claimed in claim 12 wherein the step of selecting a tubular element comprises selecting a tubular element formed by a helically wound strip, and wherein the step of manually placing said tubular element over said exterior surface of said electrode cable comprises twisting said helically wound strip around said exterior surface of said electrode cable at said selected position.

* * * * *